United States Patent [19]

Matsubara et al.

[11] Patent Number: 4,510,025

[45] Date of Patent: Apr. 9, 1985

[54] METHOD FOR PRODUCTION OF 3-SUBSTITUTED-2,2-DIMETHYLBICYCLO[2.2.1]HEPTAN-5-OLS AND ESTERS THEREOF

[75] Inventors: Yoshiharu Matsubara, Toyonaka; Tsuneaki Hirashima, Sakai; Ikuzo Nishiguchi, Hirakata, all of Japan

[73] Assignee: Kuraray Company, Ltd., Kurashiki, Japan

[21] Appl. No.: 525,898

[22] Filed: Aug. 24, 1983

[51] Int. Cl.³ .............................................. C25B 3/02
[52] U.S. Cl. ................................. 204/78; 252/522 R; 568/820
[58] Field of Search .............. 252/522 R; 204/72, 78; 568/820

[56] References Cited

U.S. PATENT DOCUMENTS 4,193,850 3/1980 Hengartner .......................... 204/72
4,233,121 11/1980 Gyori .................................... 204/78
4,312,717 1/1982 Suzukamo ............................ 204/79

*Primary Examiner*—John F. Niebling
*Attorney, Agent, or Firm*—Oblon, Fisher, Spivak, McClelland & Maier

[57] ABSTRACT

There is provided a novel method for producing 2,2-dimethyl-3-methylenebicyclo[2.2.1]heptan-5-ol and 2,2,3-trimethylbicyclo[2.2.1]heptan-3,5-diol and their lower fatty acid esters. Also provided are perfume, fragrance compositions containing 2,2-dimethyl-3-methylenebicyclo[2.2.1]heptan-5-ol or a lower fatty acid ester thereof, which has a fragrance characteristic of floral scent.

15 Claims, No Drawings

METHOD FOR PRODUCTION OF 3-SUBSTITUTED-2,2-DIMETHYLBICYCLO[2.2.1]HEPTAN-5-OLS AND ESTERS THEREOF

BACKGROUND OF THE INVENTION

1. Field of the Invention

This invention relates to a method of producing a 3-substituted-2,2-dimethylbicyclo[2.2.1]heptan-5-ol of general formula (I):

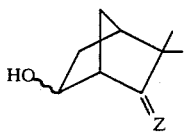

wherein Z is $=CH_2$ or

or a lower fatty acid ester thereof. More particularly, this invention relates to a method of producing a 3-substituted-2,2-dimethyl-bicyclo[2.2.1]heptan-5-ol of the above general formula or a lower fatty acid ester thereof which comprises subjecting tricyclene or/and camphene to electrolytic oxidation in a lower fatty acid and, if necessary, further subjecting the oxidation product to hydrolysis and isolating the resultant 3-substituted-2,2-dimethylbicyclo[2.2.1]heptan-5-ol of general formula (I) or lower fatty acid ester thereof.

In another aspect, this invention relates to a perfume, fragrance composition containing 2,2-dimethyl-3-methylenebicyclo[2.2.1]heptan-5-ol of general formula (I) wherein Z is $=CH_2$ or/and a lower fatty acid ester thereof.

2. Description of the Prior Art 2,2-Dimethyl-3-methylenebicyclo[2.2.1]heptan-5-ol of general formula (I) wherein Z is $=CH_2$ is a monoterpene alcohol which was isolated by Matsubara et al from the essential oil of *Chrysanthemum japonense*, and is known as nojigiku alcohol [Tetrahedron Letters No. 48, 4219-4222 (1974)]. It is known that nojigiku alcohol can be synthesized by chlorinating camphene with chlorine gas, followed by reacting the chlorinated camphene with potassium acetate, and finally hydrolyzing the obtained acetoxy-compound [D. L. Dull et al, J. Org. Chem. 29 3095 (1964)]. However, this process is not fully satisfactory from the viewpoint of yield, selectivity, etc. It is also known that camphenilane aldehyde, borneol, 2β-camphenilyl alcohol, etc. can be produced by subjecting camphene or tricyclene to electrolytic oxidation in the presence of lithium acetate as a supporting electrolyte using stainless steel electrodes [Matsubara et al, Synopsis of the 16th Symposium on the Chemistry of Terpenes, Essential Oils and Aromatics, 111-112 (1972)]. However, such electrolytic oxidation or saponification is not known to give nojigiku alcohol or an ester thereof.

Cyclic monoterpene alcohols and their esters such as borneol, isoborneol, bornyl acetate, isobornyl acetate, etc. have distinct fragrances characteristic of conifer wood and have been used for cosmetic preparations, bath preparations and toiletries, room sprays, etc. but it is not known that nojigiku alcohol is useful as a perfume, fragrance material.

It is an object of this invention to provide a novel method of producing a 3-substituted-2,2-dimethylbicyclo[2.2.1]heptan-5-ol of general formula (I) or a lower fatty acid ester thereof.

It is another object of this invention to provide a method by which nojigiku alcohol or a lower fatty acid ester thereof, which is useful as a raw material for the production of floral scent fragrances, can be easily produced.

It is still another object of this invention to provide 2,2,3-trimethylbicyclo[2.2.1]heptan-3,5-diol or a lower fatty acid ester thereof, which is a novel compound of value as a synthetic intermediate for the production of nojigiku alcohol or lower fatty acid esters thereof, and a method of producing said diol or ester thereof.

It is a further object of this invention to provide a perfume, fragrance composition containing nojigiku alcohol and/or a lower fatty acid ester thereof.

These objects as well as other objects and advantages of the present invention will become apparent to those skilled in the art from the following detailed description.

SUMMARY OF THE INVENTION

In one aspect, this invention provides a method of producing a 3-substituted-2,2-dimethylbicyclo[2.2.1]heptan-5-ol or a lower fatty acid ester thereof which comprises subjecting tricyclene and/or camphene to electrolytic oxidation in a lower fatty acid and, if necessary, further subjecting the oxidation product to hydrolysis and isolating the resultant 3-substituted-2,2-dimethylbicyclo[2.2.1]heptan-5-ol of general formula (I) or lower fatty acid ester thereof.

In another aspect, this invention provides a perfume, fragrance composition containing nojigiku alcohol or/and a lower fatty acid ester thereof.

DETAILED DESCRIPTION OF THE INVENTION

In accordance with this invention, either tricyclene or camphene or a mixture thereof is used as the substrate for electrolytic oxidation, although the contemplated compound is produced with the best selectivity when tricyclene is used as a substrate. The electrolytic oxidation is carried out in a lower fatty acid. While said lower fatty acid includes such species as acetic acid, propionic acid, butyric acid, valeric acid, etc., the use of acetic acid is particularly desirable. Since such a lower fatty acid serves not only as a solvent but also as a reactant in the electrolytic oxidation of this invention, the reaction yields an ester of 3-substituted-2,2-dimethyl-bicyclo[2.2.1]heptan-5-ol corresponding to the lower fatty acid employed. The amount of said lower fatty acid is at least about 5 moles, preferably about 20 to 100 moles per 1 mole of the substrate. It should be understood that solvents which do not interfere with the electrolytic oxidation may be additionally present in the reaction system. It is preferable that water be present in the reaction system. The presence of water in the reaction system leads to improved conductivity, thus helping reduce the required terminal voltage by a significant degree as compared with electrolytic oxidation in the absence of water and consequently enabling one to reduce the unit energy cost in a remarkable measure. The optimum amount of water to be present depends largely on the concentration of the substrate in said lower fatty acid. For example, when the concentration of the substrate is about 3 to 10 weight percent, the amount of water is about 1 to 10 weight percent, preferably about 2.5 to 5 weight percent, based on the lower fatty acid.

The electrolytic oxidation according to this invention is preferably conducted with the aid of a suitable supporting electrolyte. The supporting electrolyte is desirably an electrolyte which is inert to both the substrate and the reaction product and does not interfere with the electrolytic oxidation. Thus, it is exemplified by the halides, sulfates, phosphate, perchlorates, acetates, propionates or toluenesulfonates of alkali metals or alkaline earth metals, such as potassium chloride, magnesium sulfate, barium phosphate, lithium perchlorate, sodium perchlorate, potassium acetate, strontium acetate, potassium propionate, sodium p-toluenesulfonate, etc.; ammonium salts such as ammonium sulfate, ammonium perchlorate, ammonium acetate, ammonium propionate, ammonium p-toluenesulfonate, etc.; the halides, sulfates, phosphates, perchlorates, acetates, propionates or toluenesulfonates of primary to tertiary amines or quaternary ammonium cations having one or more alkyl groups of 1 to 6 carbon atoms, such as n-butylammonium phosphate, di-n-butylammonium acetate, triethylammonium propionate, triethylammonium chloride, triethylammonium sulfate, trimethylammonium perchlorate, tetraethylammonium p-toluenesulfonate, etc.; acyclic or cyclic amines such as trimethylamine, triethylamine, diisopropylamine, butylamine, pyrrolidine, piperazine, pyridine, picoline, etc.; and metal borohalides such as sodium fluoborate, etc. These supporting electrolytes can be used either alone or as a mixture of two or more species. Among these supporting electrolytes, lower fatty acid salts can be formed in the reaction system by adding thereto an alkali metal hydroxide, an alkaline earth metal hydroxide, aqueous ammonia, a primary to tertiary amine having a $C_{1-6}$ alkyl group or the like which is able to form a salt with the lower fatty acid present in the reaction system. Particularly desirable supporting electrolytes are amines, lower fatty acid salts and ammonium salts. The preferred amount of such supporting electrolyte depends on its species and the kind of solvent used, etc. When as the supporting electrolyte is used triethylamine, for instance, it is preferably used in an amount of 0.3 to 3.0 moles based on 1 mole of the substrate and 70 moles of acetic acid, for instance.

Since, as aforesaid, the electrolytic oxidation of this invention is carried out in a lower fatty acid, the electrode is preferably made of an acid-resistant material such as gold, platinum, titanium plated with gold or platinum, carbon, lead peroxide, etc. The electrode materials which are particularly useful in terms of reaction yield and selectivity are carbon, platinum or titanium plated with platinum. The current density may range from 5 to 100 mA/cm$^2$, preferably 10 to 50 mA/cm$^2$, and can be controlled by means of voltage tap. While the theoretical amount of electricity is 2F/mol, it is practically desirable to increase the conversion to the desired lower fatty acid ester of 3-substituted-2,2-dimethylbicyclo[2.2.1]-heptan-5-ol by employing 2.5 to 4.5F/mol of electricity. The reaction can be conducted in a comparatively broad temperature range of 10° to 50° C., for instance, but it is practically advantageous to conduct the reaction at a temperature of from 25° to 45° C. If it is desired to conduct the reaction at a fixed temperature, the reaction system may be cooled or heated by the per se conventional procedure.

The electrolytic oxidation according to this invention can be conducted continuously or batchwise. After the reaction, an oil containing the desired lower fatty acid ester of a 3-substituted-2,2-dimethylbicyclo[2.2.1]heptan-5-ol of general formula (I) can be separated from the reaction mixture by the following procedure. The reaction mixture or a residue obtainable by distilling off the unreacted substrate and the solvent from the reaction mixture under reduced pressure is poured into water or a dilute aqueous alkali solution and the mixture is then extracted with a hydrocarbon solvent such as hexane, benzene, toluene or the like. The desired lower fatty acid ester of 3-substituted-2,2-dimethylbicyclo-[2.2.1]heptan-5-ol (I) can be isolated from the above oil by the per se conventional procedure such as distillation.

The lower fatty acid ester of 3-substituted-2,2-dimethylbicyclo[2.2.1]heptan-5-ol (I) produced by electrolytic oxidation can be hydrolyzed, with or without prior isolation/purification, to give the 3-substituted-2,2-dimethylbicyclo[2.2.1]heptan-5-ol of general formula (I).

2,2,3-Trimethylbicyclo[2.2.1]heptan-3,5-diol of formula (I) wherein Z is

as well as lower fatty acid esters thereof is a novel compound which has not been described in the published literature. The lower fatty acid esters of 2,2,3-trimethylbicyclo[2.2.1]-heptan-3,5-diol are the monoesters and diesters of lower fatty acids such as, for example, the acetic acid ester, propionic acid ester, butyric acid ester, and valeric acid ester of 2,2,3-trimethylbicyclo-[2.2.1]heptan-3,5-diol. These compounds, i.e. 2,2,3-trimethylbicyclo[2.2.1]heptan-3,5-diol and its lower fatty acid esters, can be easily converted to nojigiku alcohol and its lower fatty acid esters by the per se known dehydration or elimination of carboxylic acid which is generally applied to tertiary alcohols or their esters. Typical examples of such dehydration or elimination of carboxylic acid are as follows.

(1) Dehydration or elimination of carboxylic acid at room temperature or under heating in the presence of an acid catalyst such as hydrochloric acid, phosphoric acid, boric acid, sulfuric acid, oxalic acid, acetic acid, trifluoroacetic acid, boron trifluoride-ether complex, p-toluenesulfonic acid, potassium hydrogen sulfate, silica, alumina, acidic ion exchange resin, etc.;

(2) dehydration at room temperature or under heating in the presence of a dehydrating agent such as iodine, anhydrous copper sulfate, dimethyl sulfoxide, hexamethylphosphoric triamide, phosphorus pentoxide, etc.;

(3) dehydration at a temperature of from −70° C. to an elevated temperature under heating in the presence of a halogenating agent such as thionyl chloride, phosphorus tribromide, phosphorus trichloride, phosphoryl chloride, phosphorus pentachloride, etc.; a sulfonating agent such as p-toluenesulfonyl chloride, methanesulfonyl chloride, etc.; or an esterifying agent such as acetyl chloride, acetic anhydride, etc. and preferably in the co-presence of a base such as pyridine, sodium ethoxide, potassium acetate, etc.;

(4) dehydration or elimination of carboxylic acid at a temperature of from 0° C. to an elevated temperature under heating in the presence of a base such as alkali metal hydroxides, e.g. sodium hydroxide, potassium hydroxide, etc.; amines, e.g. pyridine, dimethylaniline, 1,8-diazabicyclo[5.4.0]undecene-7, triethylamine, etc.; an alkali metal alkoxide, e.g. sodium ethoxide, potassium methoxide, potassium t-butoxide, etc.; or the lower fatty acid salts, carbonates or sulfonates of alkali metals, e.g. potassium acetate, sodium carbonate, potassium p-toluenesulfonate, etc.;

(5) elimination of carboxylic acid under heating. While these dehydration or elimination of carboxylic acid can be conducted in the absence of a solvent, it may also be conducted in the presence of a suitable solvent such as dimethylformamide, N-methylpyrrolidone, etc. In these reactions, acetic acid and amines can be used in stoichiometric excess so that they may act as solvents as well.

The 2,2,3-trimethylbicyclo[2.2.1]heptan-3,5-diol or its lower fatty acid ester which is subjected to any of the above dehydration or elimination of carboxylic acid need not have been isolated from the reaction mixture containing the same and purified. By way of example, the reaction mixture obtained by electrolytic oxidation of tricyclene is extracted with hexane or the like and the extract is washed with water and dried. The solvent is then distilled off and the residue is distilled to give the lower fatty acid ester of nojigiku alcohol, while the residual oil containing the lower fatty acid ester of 2,2,3-trimethylbicyclo[2.2.1]heptan-3,5-diol may be directly subjected to the elimination of carboxylic acid. The reaction mixture containing 2,2,3-trimethylbicyclo[2.2.1]heptan-3,5-diol which is produced by hydrolysis of the lower fatty acid ester of 2,2,3-trimethylbicyclo[2.2.1]heptan-3,5-diol can be directly subjected to the dehydration.

Nojigiku alcohol has a faint camphoraceous and minty top note and a floral note accompanied by a woody note and is of use as an olfactory component of floral perfume, fragrance compositions. Lower fatty acid esters of nojigiku alcohol also have a faint camphoraceous and minty top note and a floral note accompanied by fresh green and balsam notes and are of use as olfactory components of floral perfume, fragrance compositions. Moreover, the present inventors found that nojigiku alcohol and such lower fatty acid esters have high diffusibility and persistence and blend well with other fragrances.

Nojigiku alcohol and a lower fatty acid ester thereof can be added to perfume, fragrance compositions in their pure forms or they can be added to mixtures of materials in fragrance-imparting compositions to provide a desired fragrance character to a finished perfume material. The perfume, fragrance compositions obtained according to this invention are suitable in a wide variety of perfumed articles and can also be used to enhance, modify or reinforce natural fragrance materials. It will thus be appreciated that nojigiku alcohol and a lower fatty acid ester thereof each are useful as olfactory agents and fragrances.

The term "perfume, fragrance composition" is used herein to mean a mixture of compounds, including, for example, natural oils, synthetic oils, alcohols, aldehydes, ketones, esters, lactones, and frequently hydrocarbons which are admixed so that the combined odors of the individual components produce a pleasant or desired fragrance. Such perfume, fragrance compositions usually contain (a) the main note or the bouquet or foundation-stone of the composition, (b) modifiers which round off and accompany the main note, (c) fixatives which include odorous substances which lend a particular note to the composition throughout all stages of evaporation, and substances which retard evaporation, and (d) top notes which are usually low-boiling fresh-smelling materials. Such perfume, fragrance compositions of this invention can be used in conjunction with carriers, vehicles, solvents, dispersants, emulsifiers, surface-active agents, aerosol propellants and the like.

In perfume, fragrance compositions, the individual components contribute their particular olfactory characteristics, but the overall effect of the perfume, fragrance composition will be the sum of the effect of each ingredient. Thus, the nojigiku alcohol and a lower fatty acid ester thereof can be used alone or in combination to alter the aroma characteristics of a perfume, fragrance composition, for example, by highlighting or moderating the olfactory reaction contributed by another ingredient of the composition.

The perfume, fragrance composition according to this invention contains an olfactorily sensible amount of nojigiku alcohol and/or a lower fatty acid ester thereof. The proportion of nojigiku alcohol and/or lower fatty acid ester thereof in the total composition may vary according to the intended use of the composition; for example, it may range from about 0.0001 weight percent to 95 weight percent. The perfume, fragrance composition of this invention can be used in a large variety of ways. For example, it can be used as is, or in soaps; space deodorants; perfumes and eau de cologne; cosmetic preparations such as lotions, creams, etc.; bath supplies such as bath oil, bath salts, etc.; hair preparations such as hair tonics, pomades, hair liquids, hair creams, stick pomades, shampoos, rinses, etc.; cleansers; detergents, etc. In addition, the perfume, fragrance composition can also be used for scenting such substrates as textile fibers and fabrics, paper products and so on, and further used as flavors.

The following examples are given to merely illustrate this invention in further detail and should by no means be construed as limiting the scope of the invention.

EXAMPLE 1

1.32 g of tricyclene (GLC purity 100%) and, as a supporting electrolyte, 1.56 g of triethylamine were dissolved in 40 ml of acetic acid. The solution was put in a beaker-type undivided cell, in which it was subjected to constant current electrolysis with carbon electrodes at a current density of 20 mA/cm$^2$, a current supply of 4F/mol and a temperature of 20° to 29° C. After completion of the reaction, a large quantity of water was added to the reaction mixture and the residual acetic acid was neutralized with an aqueous solution of sodium carbonate. The solution was then extracted with 50 ml portions of n-hexane for a total of 3 times (total volume 150 ml). The extract was washed with water and dried over anhydrous sodium sulfate, followed by distillation to remove the hexane, whereby an oil was obtained. This oil was dissolved in 50 ml of methanol, followed by addition of 10 ml of 2N sodium hydroxide. The mixture was stirred at room temperature for 1.5 hours. The methanol was then distilled off from the reaction mixture under reduced pressure and the oily residue was poured into water. The mixture was extracted with 50 ml portions of n-hexane for a total of 3 times (total volume: 150 ml). The extract was washed with water, dried over anhydrous magnesium sulfate and distilled to remove the n-hexane. The above procedure gave 1.02 g of an oil wherein the FID-GLC distribution ratio of 2,2,3-trimethylbicyclo[2.2.1]heptan-3,5-diol was 8% and the FID-GLC distribution ratio of nojigiku alcohol was 57%. This oil was subjected to silica gel column chromatography to give 0.30 g of white crystals of nojigiku alcohol and 0.05 g of colorless needles of 2,2,3-trimethylbicyclo[2.2.1]heptan-3,5-diol. The physical properties of these products were as follows.

Nojigiku alcohol mp: 55°–57.5° C.
IR spectrum(cm$^{-}$): 3320, 2960, 1660, 1050, 1030, 880.
NMR spectrum (90 MHz) $\delta_{ppm}^{CDCl_3}$: 0.95, 1.02(each s, 6H); 2.61(bs, 1H); 3.7–3.9(m, 1H); 4.64, 4.85(each s, 2H).

2,2,3-Trimethylbicyclo[2.2.1]heptan-3,5-diol

IR spectrum(cm$^{-}$): 3320, 1045–1030.
Mass spectrum(m/e): 155[M—CH$_3$]$\dagger$, 152[M—H$_2$O]$\dagger$, 137[M—H$_2$O—CH$_3$]$\dagger$.
NMR spectrum (220 MHz) $\delta_{TMS}^{CDCl_3}$: 0.82, 0.89, 0.97, 1.01(each s, 6H); 1.13(s, 3H); 1.70(m, 1H); 3.9–4.2(m, 1H).

EXAMPLE 2

1.32 g of tricyclene (GLC purity 100%) was electrolytically oxidized in the same manner as Example 1 and the reaction mixture was further treated as in Example 1 to give 1.21 g of an oil in which the FID-GLC distribution ratio of 2,2,3-trimethylbicyclo-[2.2.1]heptan-3,5-diol diacetate was 10% and the FID-GLC distribution ratio of nojigiku alcohol acetate was 61%. This oil was subjected to silica gel column chromatography to give 0.56 g of nojigiku alcohol acetate and 0.08 g of 2,2,3-trimethylbicyclo-[2.2.1]heptan-3,5-diol diacetate. The physical properties of these products were as follows.

Nojigiku alcohol acetate

IR spectrum(cm$^{-1}$): 2980, 1740, 1660, 1380, 1250, 1230, 1030, 890.
NMR spectrum(90 MHz) $\delta_{ppm}^{CDCl_3}$: 0.98, 1.02(each s, 6H); 2.00(s, 3H); 2.75(bs, 1H); 4.5–4.7(m, 1H); 4.70, 4.95(each s, 2H).

2,2,3-Trimethylbicyclo[2.2.1]heptan-3,5-diol diacetate

IR spectrum(cm$^{-1}$): 1740.
Mass spectrum(m/e): 152[M—CH$_3$COO—CH$_3$CO]$\dagger$, 137[M—CH$_3$COO—CH$_3$CO—CH$_3$]$\dagger$.
NMR spectrum(90 MHz) $\delta_{HMS}^{CCl_4}$: 0.92, 1.03(each s, 6H); 1.47(s, 3H); 1.90, 1.94(each s, 6H); 2.72(bs, 1H); 4.6–4.8(m, 1H).

EXAMPLE 3

1.36 g of tricyclene (GLC purity 100%) and, as a supporting electrolyte, 2.50 g of tetraethylammonium p-toluenesulfonate were dissolved in 40 ml of acetic acid. The solution was put in a beaker-type undivided cell, in which constant current electrolysis was carried out using carbon electrodes at a current density of 10 mA/cm$^2$, a current supply of 4F/mol and a temperature of 20° to 29° C. After completion of the reaction, the acetic acid was distilled off under reduced pressure at about 40° C. and the acetic acid remaining in a very small amount was neutralized with an aqueous solution of potassium carbonate. The solution was then extracted with 50 ml portions of n-hexane for a total of 3 times (total volume 150 ml). The extract was washed with water, dried over anhydrous magnesium sulfate and distilled to remove the hexane, whereby 1.25 g of an oil was obtained. This oil was dissolved in 50 ml of ethanol, followed by addition of 10 ml of 2N sodium hydroxide. The mixture was refluxed for 1.5 hours. The ethanol was distilled off under reduced pressure and the residue was poured into water and extracted with n-hexane. The extract was washed with water and dried over anhydrous magnesium sulfate. Removal of the solvent by distillation gave 1.02 g of crude nojigiku alcohol with an FID-GLC distribution ratio of 57%. This crude nojigiku alcohol was recrystallized from ethanol to recover 0.30 g of nojigiku alcohol as white crystals melting at 55°–57.5° C. The physical properties of this product were in agreement with those of the nojigiku alcohol obtained in Example 1.

EXAMPLE 4

1.32 g of tricyclene (GLC purity 100%) and, as a supporting electrolyte, 1.56 g of triethylamine were dissolved in 40 ml of acetic acid. This solution was put in a beaker-type undivided cell, in which constant current electrolysis was carried out using carbon electrodes at a current density of 10 mA/cm$^2$, a current supply of 4F/mol and a temperature of 20°–29° C. After completion of the reaction, the product mixture was treated in the same manner as Example 3 to give 1.25 g of an oil. This oil was hydrolyzed and distilled as in Example 3 to recover 0.98 g of crude nojigiku alcohol with an FID-GLC distribution ratio of 57%. This crude nojigiku alcohol was recrystallized from ethanol to give 0.51 g of nojigiku alcohol as white crystals.

EXAMPLE 5

2.72 g of camphene (GLC purity 100%) and, as a supporting electrolyte, 5.02 g of tetraethylammonium p-toluenesulfonate were dissolved in 80 ml of acetic acid, and the solution was put in a beaker-type undivided cell, in which constant current electrolysis was carried out using carbon electrodes at a current density of 10 mA/cm$^2$, a current supply of 4F/mol, and a temperature of 29° C. The reaction mixture was further treated as in Example 1 to give 2.62 g of an oil. This oil was hydrolyzed and distilled in the same manner as Example 1 to recover 2.65 g of crude nojigiku alcohol with an FID-GLC distribution ratio of 19%. This crude nojigiku alcohol was recrystallized from ethanol to give 0.43 g of nojigiku alcohol as white crystals.

EXAMPLE 6

In the same manner as Example 3, 1.36 g of tricyclene (GLC purity 100%) was subjected to electrolytic oxidation and the reaction mixture was extracted to give 1.30 g of an oil containing nojigiku alcohol acetate. This oil was distilled under reduced pressure to give 0.73 g of nojigiku alcohol acetate as a fraction boiling at 98° C./7 mmHg. The physical properties of this product were in agreement with those of the nojigiku alcohol acetate obtained in Example 2.

EXAMPLE 7

The electrolytic oxidation according to Example 3 was repeated except that 40 ml of propionic acid was used in lieu of 40 ml of acetic acid. The reaction mixture was then extracted as in Example 3 to obtain 1.32 g of an oil containing nojigiku alcohol propionate. This oil was distilled under reduced pressure to recover 0.81 g of nojigiku alcohol propionate as a fraction boiling at 101° C./7 mmHg. The physical properties of this product were as follows.

IR spectrum(cm$^{-1}$): 2980, 1740, 1660, 1180, 1020, 890.

NMR spectrum (90 MHz) $\delta_{ppm}^{CDCl_3}$: 1.00, 1.04(each s, 6H); 1.10(t, 3H); 2.27(q, 2H); 2.75(bs, 1H); 4.5–4.7(m, 1H); 4.70, 4.96(each s, 2H).

EXAMPLES 8 TO 12

A beaker-type undivided cell was charged with tricyclene (GLC purity 92.2%, camphene content 1.3%), acetic acid, water and supporting electrolyte in the amounts indicated in Table 1 and constant current electrolysis was carried out using carbon electrodes at a current density of 35 mA/cm$^2$, a current supply of 2.5F/mol, and a temperature of 22°–30° C. After completion of the reaction, the reaction mixture was treated in the same manner as Example 2 to give an oil. The nojigiku alcohol acetate and 2,2,3-trimethylbicyclo[2.2.1]heptan-3,5-diol diacetate contained in this oil were determined by FID-GLC. The results are shown in Table 1.

TABLE 1

| Example | Tricyclene (g) | Acetic acid (ml) | Water (ml) | Supporting electrolyte | Output of nojigiku alcohol acetate (% yield) | Output of 2,2,3-trimethylbicyclo [2.2.1]-heptan-3,5-diol diacetate (% yield) |
|---|---|---|---|---|---|---|
| 8 | 0.25 | 10 | 0.25 | Potassium acetate, 0.25 g | 58.0 | 2.7 |
| 9 | 0.25 | 10 | — | Aqueous ammonia (25%), 0.36 ml | 59.3 | 6.7 |
| 10 | 0.25 | 10 | — | Trisodium phosphate. 12 H$_2$O, 1.0 g | 53.1 | 9.1 |
| 11 | 0.25 | 10 | 0.25 | Lithium perchlorate. 3 H$_2$O, 0.42 g | 48.7 | 6.6 |
| 12 | 0.15 | 13 | 3.00 | Ammonium sulfate, 0.35 g | 57.1 | 3.4 |

REFERENCE EXAMPLE 1

15.0 g of 2,2,3-trimethylbicyclo[2.2.1]heptan-3,5-diol diacetate was refluxed in 100 ml of acetic acid for 15 hours. The resultant reaction mixture was poured into water and extracted with n-hexane. The extract was washed with water and an aqueous solution of sodium hydrogen carbonate in the order mentioned, dried over anhydrous magnesium sulfate and distilled to remove the hexane. The residue was further distilled under reduced pressure to recover 10.9 g of nojigiku alcohol acetate as a fraction boiling at 98° C./7 mmHg. The physical properties of this product were in agreement with those of the nojigiku alcohol acetate obtained in Example 2.

REFERENCE EXAMPLE 2

In 5.0 ml of pyridine was dissolved 1.7 g of 2,2,3-trimethylbicyclo[2.2.1]heptan-3,5-diol and, then, 1.2 g of thionyl chloride was added dropwise to the solution at a temperature of −5° C. to 0° C. The mixture was stirred for 2 hours, after which it was poured into water and extracted with n-hexane. The extract was washed with dilute hydrochloric acid and an aqueous solution of sodium hydrogen carbonate in that order, dried over anhydrous magnesium sulfate, and distilled to remove the hexane. The residue was subjected to silica gel column chromatography to give 0.10 g of nojigiku alcohol. The physical properties of this product were in agreement with those of the nojigiku alcohol obtained in Example 1.

EXAMPLE 13

Woody perfume composition

A perfume composition having a woody note was prepared according to the following formula.

|  | Parts by weight |
|---|---|
| Sandalwood oil | 50 |
| Vetiver oil | 50 |
| Cedarwood oil | 100 |
| Ionone α | 250 |
| Methyl ionone | 120 |
| Phenylethyl alcohol | 50 |
| Benzyl acetate | 50 |
| Citronellol | 30 |
| Coumarin | 50 |
| Bergamot oil | 20 |
| Iris liquid | 20 |
| Ylang-ylang oil | 40 |
| Octyl acetate | 10 |
| Cedryl acetate | 10 |
| Musk ambrette | 50 |
| Nojigiku alcohol | 80 |
| Nojigiku alcohol acetate | 20 |
|  | 1000 |

EXAMPLE 14

Chypre type perfume composition

A perfume composition having a chypre note was prepared according to the following formula.

|  | Parts by weight |
|---|---|
| Bergamot oil | 200 |
| Neroli absolute | 20 |
| Linalool | 50 |
| Linalyl acetate | 30 |
| Amyl salicylate | 50 |
| Benzyl acetate | 80 |
| Oak moss oil | 50 |
| Phenylethyl alcohol | 60 |
| Methyl ionone | 40 |
| Lily aldehyde | 20 |
| Eugenol | 30 |
| Terpineol | 50 |
| Sandalwood oil | 50 |
| Coumarin | 50 |
| Vanillin | 30 |
| Musk ambrette | 70 |
| Rose absolute | 10 |
| Jasmin absolute | 10 |
| Benzoin | 20 |

| | Parts by weight |
|---|---|
| Nojigiku alcohol acetate | 80 |
| | 1000 |

EXAMPLE 15

Fresh green type perfume composition

A perfume composition having a fresh green note was prepared according to the following formula.

| | Parts by weight |
|---|---|
| Phenylethyl alcohol | 200 |
| Hydroxycitronellal | 150 |
| Cedarwood oil | 100 |
| Geranium oil | 50 |
| Methylphenylcarbinyl acetate | 50 |
| Terpineol 100 | |
| Citronellol | 10 |
| Hiba oil | 20 |
| Lily aldehyde | 100 |
| Linalyl acetate | 50 |
| Nojigiku alcohol | 50 |
| Nojigiku alcohol propionate | 120 |
| | 1000 |

EXAMPLE 16

Green-mossy-aldehyde type perfume composition

A perfume composition having a green-mossy-aldehyde note was prepared according to the following formula

| | Parts by weight |
|---|---|
| Linalool | 50 |
| Linalyl acetate | 70 |
| Oak moss oil | 40 |
| Aldehyde C-10 10% | 20 |
| Aldehyde C-12 (MNA) 10% | 20 |
| Methylphenylcarbinyl acetate | 30 |
| Citronellol | 50 |
| Geraniol | 50 |
| Nerol | 30 |
| Methyl ionone | 100 |
| Phenylethyl alcohol | 80 |
| Hydroxycitronellal | 50 |
| Patchouli oil | 20 |
| Hexylcinnamic aldehyde | 140 |
| Opopanax | 20 |
| Sandalwood oil | 30 |
| Bergamot oil | 80 |
| Chamomile oil | 20 |
| Nojigiku alcohol | 50 |
| Nojigiku alcohol propionate | 50 |
| | 1000 |

EXAMPLE 17

Fresh green woody type perfume composition

A perfume composition having a fresh green woody note was prepared according to the following formula.

| | Parts by weight |
|---|---|
| Estragon oil | 50 |
| Patchouli oil | 20 |
| Phenylethyl alcohol | 100 |
| Hydroxycitronellal | 50 |
| Methyl jasmonate | 150 |

| | Parts by weight |
|---|---|
| Linalool | 80 |
| Linalyl acetate | 50 |
| Citronellol | 50 |
| Geraniol | 70 |
| Methyl ionone | 50 |
| Galbanum oil | 30 |
| Clary sage oil | 20 |
| Costus root oil | 10 |
| Aldehyde C-12 (MNA) 10% | 10 |
| Aldehyde C-10 10% | 10 |
| Coumarin | 30 |
| Vetiver oil | 40 |
| Musk ambrette | 30 |
| Musk tinc. | 20 |
| Nojigiku alcohol | 50 |
| Nojigiku alcohol acetate | 80 |
| | 1000 |

EXAMPLE 18

Modern woody type perfume composition

A perfume composition having a modern woody note was prepared according to the following formula.

| | Parts by weight |
|---|---|
| Hyacinth absolute | 50 |
| Ylang-ylang oil | 50 |
| Neroli oil | 30 |
| Linalool | 70 |
| Citronellyl oxyacetaldehyde | 150 |
| Amyl salicylate | 70 |
| Aldehyde C-12 (MNA) 10% | 50 |
| Methyl jasmonate | 80 |
| Sandalwood oil | 70 |
| Coumarin | 50 |
| Musk ambrette | 40 |
| Amber tinc. | 30 |
| Benzyl salicylate | 50 |
| Tuberose absolute 10% | 30 |
| Heliotropin | 30 |
| Nojigiku alcohol | 50 |
| Nojigiku alcohol propionate | 100 |
| | 1000 |

What is claimed is:

1. A method of producing a 3-substituted-2,2-dimethylbicyclo[2.2.1]heptan-5-ol of general formula

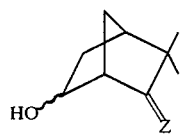

(I)

wherein Z is $=CH_2$

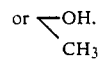

a lower fatty acid ester thereof, or a combination thereof, which comprises subjecting tricyclene, camphene, or a mixture thereof to electrolytic oxidation in a lower fatty acid and isolating the resultant 3-substituted-2,2-dimethylbicyclo[2.2.1]heptan-5-ol, lower fatty acid ester thereof, or combination thereof.

2. A method as claimed in claim 1 wherein said lower fatty acid is acetic acid.

3. A method as claimed in claim 1 wherein the amount of said lower fatty acid is at least about 5 moles per 1 mole of tricyclene, camphene, or a mixture thereof.

4. A method as claimed in claim 1 wherein the amount of said lower fatty acid is about 20 to 100 moles per 1 mole of tricyclene, camphene, or a mixture thereof.

5. A method as claimed in claim 1 wherein said electrolytic oxidation is carried out in the presence of water.

6. A method as claimed in claim 1 wherein said electrolytic oxidation is carried out using an amine, lower fatty acid salt, ammonium salt, or combination thereof as supporting electrolyte.

7. A method as claimed in claim 1 wherein said electrolytic oxidation is carried out using carbon electrodes.

8. A method as claimed in claim 1 further comprising subjecting the oxidation product to hydrolysis prior to isolation of the resultant 3-substituted-2,2-dimethylbicyclo[2.2.1]heptan-5-ol, lower fatty acid ester thereof, or combination thereof.

9. A method as claimed in claim 5 wherein said electrolytic oxidation is carried out in the presence of about 1 to 10 weight percent of water.

10. A method as claimed in claim 9 wherein said electrolytic oxidation is carried out in the presence of about 2.5 to 5 weight percent of water.

11. A method as claimed in claim 1 wherein said electrolytic oxidation is carried out using acid resistant electrodes comprising gold electrodes, platinum electrodes, titanium electrodes plated with gold, titanium electrodes plated with platinum, lead peroxide electrodes, or a mixture thereof.

12. A method as claimed in claim 1 wherein the reaction temperature is about 10° C. to 50° C.

13. A method as claimed in claim 12 wherein the reaction temperature is about 25° C. to 40° C.

14. A method as claimed in claim 1 wherein the reaction is run continuously.

15. A method as claimed in claim 1 wherein the reaction is run batchwise.

* * * * *